United States Patent [19]

Jones

[11] Patent Number: 4,635,281
[45] Date of Patent: Jan. 6, 1987

[54] MEANS FOR COUNTING DROPS

[76] Inventor: J. Paul Jones, R.D. 1 Box 171-C, Glenmoore, Pa. 19343

[21] Appl. No.: 674,406

[22] Filed: Nov. 23, 1984

[51] Int. Cl.$^4$ .......................... G02B 5/14; A61M 5/16
[52] U.S. Cl. ..................................... 377/21; 250/577; 604/253
[58] Field of Search .......................... 377/21; 250/577; 604/251, 253

[56] References Cited

U.S. PATENT DOCUMENTS

| | | | |
|---|---|---|---|
| 4,270,049 | 5/1981 | Tanaka et al. | 250/577 |
| 4,432,762 | 2/1984 | Dawe | 604/253 |
| 4,443,699 | 4/1984 | Keller | 250/577 |
| 4,496,351 | 1/1985 | Hiller et al. | 604/253 |

Primary Examiner—John S. Heyman
Attorney, Agent, or Firm—Frederick J. Olsson

[57] ABSTRACT

A light source to project a light beam along an axis to a receiver means intermediate the source and the receiver to cause the light to refract so that the light reaching the receiver is substantially reduced; means to periodically introduce a quantity of liquid into the area where the light is refracted, the liquid changing the amount of refraction whereby the light reaching said receiver is substantially increased; and means to detect each said change in light at said receiver and count same.

4 Claims, 5 Drawing Figures

MEANS FOR COUNTING DROPS

This invention relates in general to fluid systems which are charged on a drop-by-drop basis. More particularly, the invention relates to an improved method and equipment for use at the entry point in such systems to accurately count the number of drops entering the system.

The invention contemplates such drop-counting by providing a drop-conducting, light refractive gap and projecting a light beam from a source through the drop-conducting gap to a receiver with the refractive gap functioning to cut off the light beam in the absence of a drop. Then after causing a drop of fluid to enter and flow through the gap, changing the amount of refraction so that the light beam at the receiver is substantially increased; and detecting each such change to count the number of drops.

The invention finds special utility in medical intervenous infusion systems and will be explained in that connection. It will be understood, however, that the invention is useful for other systems which are charged on a drop-by-drop basis.

The invention will be explained below in connection with the following drawings wherein.

Figure 1:
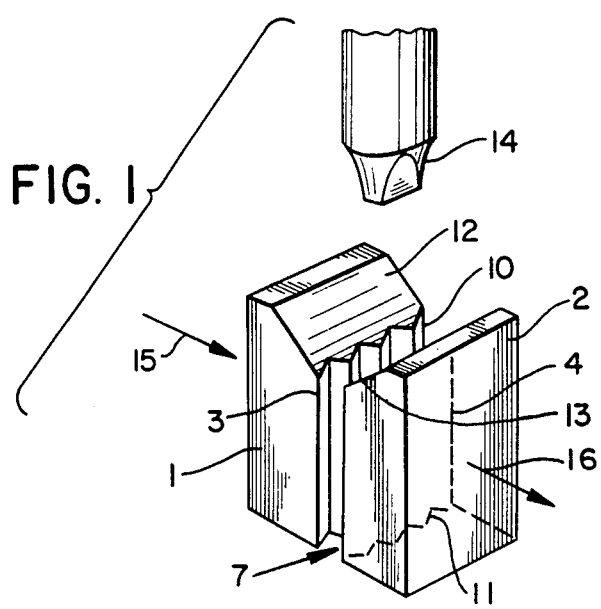
FIG. 1 is perspecitve diagramatic view to illustrate the gap means of the invention.

In FIG. 1 I have diagramatically illustrated the drop-conducting, light refractive gap of the invention.

The elongated members 1 and 2 are made of light-conducting material. Each of the members 1 and 2 has a gap surface, the gap surface for the member 2 being indicated at 4. The members 1 and 2 extend in a generally vertical direction with the gap surfaces 3 and 4 facing one another and generally parallel. The facing surfaces 3 and 4 form a vertically extending gap 7.

Each gap surface is formed as a light refracting grating, that has a plurality of vertically extending planar surfaces 10 and 11 with respect to a horizontal plane which are part of the vertical gap surfaces 2 and 3.

At the top end of the gap 7, each member is formed with a slanted surface such as the surface 12 for the member 1 and the surface 13 for the member 2. The slanted surfaces 12 and 13 face one another and form a guide to receive drops of fluid and direct same into the gap 7. A means above the gap is arranged to carry a body of fluid and cause the same to move downwardly drop-by-drop through the discharge means 14 from which the drop moves down into the slanted surfaces 12 and 13 and thence into the gap 7 and down through the gap and out of the bottom end.

Below the members 1 and 2 a reservoir or other like means is located to receive the drops discharged from the gap.

The dimensions of the members 1 and 2 and particularly the surfaces 10, 11, 12, and 13 and the material from which the members 1 and 2 are formed are chosen with the following criteria in mind.

The capillary forces of the guide surfaces 10 and 11 cause the fluid in the guide to be attached thereto vis-a-vis the cohesive forces or surface tension of the fluid so that the drop moves down the guide under the influence of gravity as a unitary mass and does not spill over the sides. The drop goes down the guide intact. Likewise, the surface tension forces of the surfaces 12 and 13 guide the drop down through the gap as a unitary mass and into the sides of the gap. The drop then goes down the gap intact. The foregoing is attained in a typical gap discussed below. It will be understood that the dimensions given are approximate.

For use in drip chambers of an intervenous feeding system the members 1 and 2 are made of material preferably an acrylic or clear polyvinyl chloride. Each member has a height of 1", a thickness of 3/16", and a width of ⅜". The width of each planar surface 11 is 0.015" and the distance between peaks of these surfaces is 0.030". The surfaces are oriented at approximately 45° or 90° to each other. There are 5 peaks across the surface. The same dimensions apply to the planar surfaces 12.

The guide surfaces 10 and 11 and the planar surfaces 12 and 13 are formed by molding the material. The finish of each of the surfaces should be polished to give glass-like clarity.

When using the gap mechanism in a drop counting system a light beam is formed to project (as noted by arrows 15 and 16) through the member 1, through the gap 7, and through the member 2 (or vice-versa).

The manner in which the light beam is refracted and particularly change in refraction will be commented on in connection with the use of the gap mechanism in a drip chamber to count the drops entering same.

Figure 2:
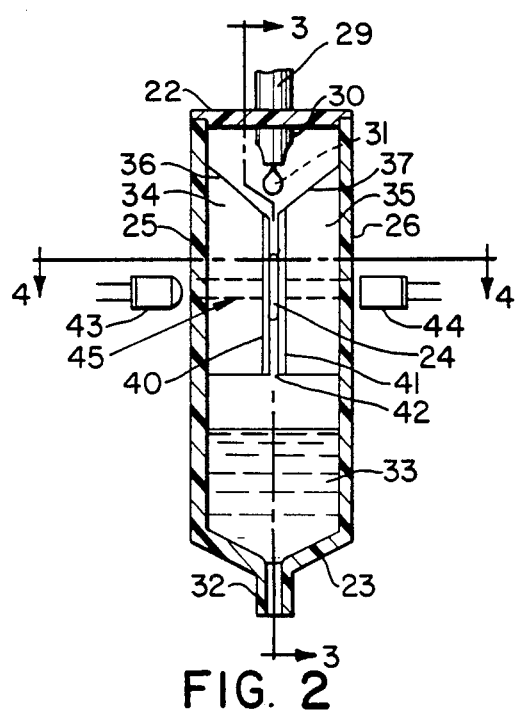
FIG. 2 is an elevational view taken along the lines 2—2 of FIG. 3.
Figure 3:
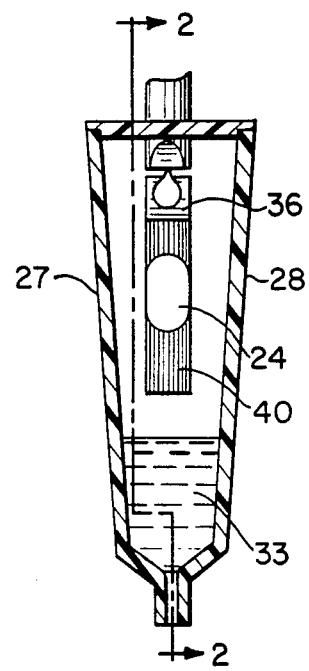
FIG. 3 is an elevational view taken along the lines 3—3 of FIG. 2.

Referring to FIGS. 2 and 3, a drip chamber 20 comprises a hollow, generally vertically extending housing having a top wall 22, a bottom wall 23, and side walls 25 and 26. There are also a pair of adjacent walls 27 and 28. The walls 25 and 26 are flat, of uniform thickness, and extend parallel one another. The various walls are preferably made as one piece by molding.

The top wall 22 is part of the connection spike 29 which is connected to the source of fluid and has means for regulating the drip flow. A drop which exits from the ejector nozzle valve 30 is noted at 31.

The bottom wall has a discharge nozzle 32 which is connected to the flexible tubing going to the patient. The fluid in the chamber is indicated at 33.

The elongated members (similar to members 1 and 2) forming the gap are indicated at 34 and 35. The member 34 is integral with the wall 25 and the member 35 is integral with the wall 26.

The members 34 and 35 respectively have slanted surfaces 36 and 37 with the equivalent slanted surfaces 12 and 13 together with gap surfaces 40 and 41 which are the equivalent of gap surfaces 3 and 4 in FIG. 1 and form gap 42.

A drop 31 exiting from the ejector nozzle/valve 30 falls on the slanted surfaces 36 and 37 and then goes into the gap 42. The drop in the gap 42 is indicated at 24.

Adjacent to the member 25 is a light source 43 which is a conventional infra-red light emitting diode and adjacent to the member 26 is a light receiver 44 which is a conventional phototransistor.

The light source is arranged to form and project a beam 45 through the wall 25, through the member 34, through the gap 42, through the member 35, through the wall 26 to the receiver 44.

Figures 4, 5:
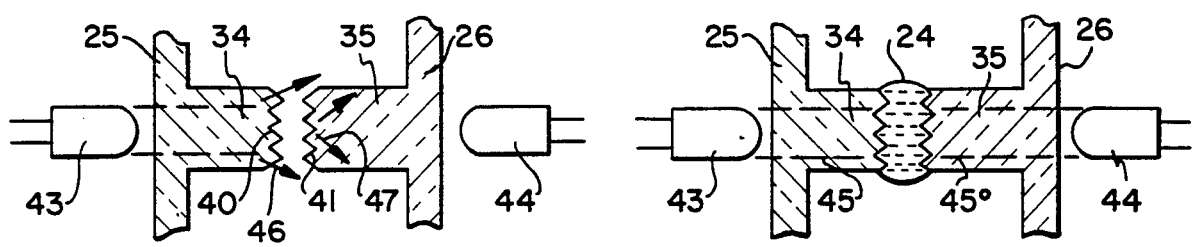
FIG. 4 is a fragmentary plan view looking along the lines 4—4 of FIG. 2.
FIG. 5 is a view similar to FIG. 4.

The functioning of the gap surfaces and the drop to effect change in refraction of the beam 45 will next be described, particularly with reference to FIGS. 4 and 5.

The planar surfaces of each gap are oriented at approximately 45° angles to the direction of propogation of the beam. Thus, some of the rays of the beam projected on the gap surface 40 are refracted outwardly as indicated by the arrows 46 in FIG. 4. Some of the rays will not reach the surface 41 but some of those that do will also be refracted again as indicated by the arrows 47. Some remaining rays will reach the light receiver 44. The receiver 44 generates a d.c. signal which is constant so long as the amount of light remains constant across the empty gap 42.

When a drop of fluid such as the drop 24 reaches the area where the light is being refracted by surfaces 40 and 41, it provides an entirely different medium (gas vs. liquid) in contact with the surfaces 40 and 41 the affect of which is to cause the amount of refraction to be greatly reduced. The intensity of the beam or the amount of light passing through the member 35 and into the receiver 44 is thereby increased. This is diagramatically indicated at 45a. The receiver 44 generates a signal which is of much greater magnitude than the first said signal.

It will be readily apparent that the change in signal is a function of the appearance of a drop in the refraction area. The number of changes is equal to the number of drops. For counting the drops the receiver 44 is connected to a standard counter 50 which is generally a small solid state variety.

With a gap to the kind described, light transmission ratio is approximately 3:1, that is to say that the light going to the receiver with a drop in the gap is approximately three times the light going to the receiver without a drop in the gap, which is an excellent ratio for accurate differentiation of pulse or no pulse, representing drop or no drop.

I claim:

1. For use with means to permit a body of clear fluid to move downwardly drop by drop, mechanism to count the number of drops comprising:
   a pair of elongated members made of light conducting material;
   on each said member, a gap surface formed as a light refractive grating;
   means supporting said members to extend in a generally vertical direction with said gap surfaces facing one another to form a generally vertically extending gap;
   each member, at the top end of said gap, being formed with a slanted surface, the slanted surfaces facing one another and forming a guide to receive each of said drops and direct each drop into said gap;
   said slanted guide surfaces attracting the fluid of a drop impinging thereon with the attraction forces between the fluid and the slanted surfaces and the cohesive force of the fluid, providing that the fluid moves down through the guide as a unitary mass into the gap under the influence of gravity;
   said gap surfaces attracting the fluid of the drop entering the gap with the attraction forces between the fluid and gap surfaces providing that the fluid moves down as a unitary mass through the gap under the influence of gravity;
   a light source adjacent to one of said members and a light receiver adjacent to the other of said members, the light source being oriented to project a beam of light through said first member, through said gap, through said second member, and thence to said light receiver;
   said gap surfaces, in the absence of said liquid therebetween, refracting the light from the source so that the quantum of light received by the light receiver is less than the quantum of light from the source, and with the presence of said liquid between said gap surfaces changing the amount of said refraction whereby the quantum of light received by the receiver is substantially increased, said increase in light reaching the receiver signifying the presence or absence of a drop in said gap; and
   means connected to said receiver and operative as a function of said change in light to count the number of changes and thereby count the number of drops passing through said gap.

2. Mechanism for use with means to permit body of clear fluid to move downwardly drop by drop, the mechanism comprising:
   a pair of elongated members made of light-conducting material;
   on each said member, a gap surface formed as a light refractive grating;
   on each member, supporting means supporting the member to extend in a generally vertical direction and respectively supporting the members with said gap surfaces facing one another to form a generally vertically extending gap;
   said supporting means for each elongated member being connected to its member at least in an area opposite the gap surface and in the connection area being integral with the member and being made of light-conducting material;
   each member, at the top end of said gap, being formed with a slanted surface, the slanted surfaces facing one another and forming a guide to receive each of said drops and direct each drop into said gap;
   said slanted surfaces attracting the fluid of a drop impinging thereon with the attraction forces between the fluid and the slanted surfaces and the cohesive force of the fluid providing that the fluid move down through the guide as a unitary mass into the gap under the influence of gravity; and
   said gap surfaces attracting the fluid of the drop entering the gap with the attraction force between the fluid and gap surfaces providing that the fluid moves down as a unitary mass through the gap under the influence of gravity.

3. A method of detecting the presence of a clear liquid medium:
   forming and projecting a light beam along an axis from a source of light to a receiver of light;
   intermediate said source and said receiver, causing the light to refract so that the light reaching the receiver is substantially reduced;
   periodically introducing a quantity of liquid into the area where the light is refracted, the liquid changing the amount of refraction whereby the light reaching said receiver is substantially increased; and
   detecting each said change in light at said receiver and counting each change.

4. In a drip chamber for a medical infusion system:
   a hollow, generally vertically extending housing having a top wall, a bottom wall, and a side wall which form a chamber, the side wall including first and second flat walls of uniform thickness which are parallel to one another and the parallel walls being made of light conducting material;

means on said top wall permitting clear fluid to fall, drop after drop, into said chamber;

means on said bottom wall permitting fluid in the chamber to exit therefrom;

a first elongated member of said chamber and integral with said first parallel wall and made of the same material as said first parallel wall;

a second elongated member inside of said chamber and integral with said second parallel wall and made of the same material as said second parallel wall;

on each said member, a gap surface formed as a light refractive grating and the respective gap surfaces facing one another to form a generally vertically extending gap;

each member, at the top end of said gap, being formed with a slanted surface, the slanted surfaces facing one another and forming a guide to receive each of said drops and direct each drop into said gap;

said slanted surfaces attracting the fluid of a drop impinging thereon with the attraction forces between the fluid and the slanted surfaces and the cohesive force of the fluid providing that the fluid move down through the guide as a unitary mass into the gap under the influence of gravity;

said gap surfaces attracting the gluid of the drop entering the gap with the attraction force between the fluid and gap surfaces and the cohesive force of the fluid providing that the fluid moves down as a unitary mass through the gap under the influence of gravity;

a light source adjacent said first parallel wall and a light receiver adjacent said second parallel wall, the light source being oriented to project a beam of light through said parallel wall, through said first member, through said gap, through said second member, through said second parallel wall, and thence to said light receiver;

said gap surfaces, in the absence of said liquid therebetween, refracting the light from the source so that the quantum of light received by the light receiver is less than the quantum of light from the source and the presence of said liquid between said gap surfaces changng the amount of said refraction whereby the quantum of light received by the receiver is increased, said change in light reaching the receiver signifying the presence or absence of a drop in said gap; and means connected to said receiver and operative as a function of said change in light to count the number of changes and thereby count the number of drops passing through said gap.

* * * * *